(12) United States Patent
Huang et al.

(10) Patent No.: US 10,512,495 B2
(45) Date of Patent: Dec. 24, 2019

(54) METHOD FOR FABRICATING MEDICAL DEVICE AND APPLICATIONS THEREOF

(71) Applicant: INDUSTRIAL TECHNOLOGY RESEARCH INSTITUTE, Hsinchu (TW)

(72) Inventors: Wei-Chin Huang, Tainan (TW); Chuan-Sheng Chuang, Tainan (TW); Ching-Chih Lin, Tainan (TW); De-Yau Lin, Tainan (TW); Sung-Ho Liu, Kaohsiung (TW); I-Chun Lai, Tainan (TW)

(73) Assignee: INDUSTRIAL TECHNOLOGY RESEARCH INSTITUTE, Chutung, Hsinchu (TW)

( * ) Notice: Subject to any disclaimer, the term of this patent is extended or adjusted under 35 U.S.C. 154(b) by 119 days.

(21) Appl. No.: 15/857,185

(22) Filed: Dec. 28, 2017

(65) Prior Publication Data

US 2019/0201065 A1   Jul. 4, 2019

(51) Int. Cl.
*A61B 17/86* (2006.01)
*A61L 31/14* (2006.01)
(Continued)

(52) U.S. Cl.
CPC .......... *A61B 17/866* (2013.01); *A61L 31/022* (2013.01); *A61L 31/026* (2013.01);
(Continued)

(58) Field of Classification Search
CPC .............................. A61B 17/866; B33Y 70/00
See application file for complete search history.

(56) References Cited

U.S. PATENT DOCUMENTS 3,678,925 A   7/1972   Fischer et al.
3,687,135 A   8/1972   Stroganov et al.
(Continued)

FOREIGN PATENT DOCUMENTS

AU   2002354914 B2   3/2003
CN      1290181 A     4/2001
(Continued)

OTHER PUBLICATIONS

Checkik, Ofir, et al., "Favorable radiographic outcomes using the expandable proximal femoral nail in the treatment of hip fractures—A randomized controlled trial," Journal of Orthopaedics II, 2014, pp. 103-109, Reed Elsevier India Pvt. Ltd., Tel Aviv, Israel.
(Continued)

*Primary Examiner* — Christian A Sevilla
(74) *Attorney, Agent, or Firm* — Muncy, Geissler, Olds & Lowe, P.C.

(57) ABSTRACT

A method for fabricating a medical device includes steps as follows: A degradable powder including at least one metal element is firstly provided on a target surface. A focused energy light bean is applied to sinter/cure the biodegradable powder within an oxygen-containing atmosphere; wherein the oxygen concentration of the oxygen-containing atmosphere is adjusted to provide a first oxygen concentration and a second concentration when the focused energy light is driven to a first location and second location of the target surface respectively. The aforementioned processes are then repeatedly carried out to form a three-dimensional (3D) structure of the medical device.

19 Claims, 6 Drawing Sheets

(51) Int. Cl.
*A61L 31/02* (2006.01)
*B33Y 70/00* (2015.01)
*B33Y 80/00* (2015.01)
*A61B 17/80* (2006.01)
*A61B 17/00* (2006.01)
*B22F 3/105* (2006.01)
*B28B 1/00* (2006.01)
*B33Y 10/00* (2015.01)
*A61B 17/84* (2006.01)

(52) U.S. Cl.
CPC .............. *A61L 31/148* (2013.01); *B33Y 70/00* (2014.12); *B33Y 80/00* (2014.12); *A61B 17/80* (2013.01); *A61B 17/846* (2013.01); *A61B 2017/00526* (2013.01); *B22F 3/1055* (2013.01); *B22F 2301/058* (2013.01); *B22F 2301/30* (2013.01); *B28B 1/001* (2013.01); *B33Y 10/00* (2014.12)

(56) References Cited

U.S. PATENT DOCUMENTS

| | | |
|---|---|---|
| 4,432,358 A | 2/1984 | Fixel |
| 4,632,101 A | 12/1986 | Freedland |
| 4,721,103 A | 1/1988 | Freedland |
| 4,862,883 A | 9/1989 | Freeland |
| 5,032,125 A | 7/1991 | Durham et al. |
| 5,182,170 A | 1/1993 | Marcus et al. |
| 5,197,971 A | 3/1993 | Bonutti |
| 6,215,093 B1 | 4/2001 | Meiners et al. |
| 6,287,332 B1 | 9/2001 | Bolz et al. |
| 6,554,833 B2 | 4/2003 | Levy et al. |
| 6,648,890 B2 | 11/2003 | Culbert et al. |
| 6,783,530 B1 | 8/2004 | Levy |
| 6,814,926 B2 | 11/2004 | Geving et al. |
| 6,823,928 B2 | 11/2004 | Sercombe et al. |
| 6,848,494 B2 | 2/2005 | Newell et al. |
| 7,601,152 B2 | 10/2009 | Levy et al. |
| 8,236,046 B2 | 8/2012 | Weber |
| 8,372,144 B2 | 2/2013 | Mueller et al. |
| 8,435,281 B2 | 5/2013 | Weber |
| 8,545,572 B2 | 10/2013 | Olson |
| 8,668,732 B2 | 3/2014 | Scheuermann et al. |
| 9,138,274 B1* | 9/2015 | Biesinger ........... A61B 17/7225 |
| 9,402,669 B2 | 8/2016 | Neubert et al. |
| 9,510,932 B2 | 12/2016 | Kumta et al. |
| 9,662,123 B2* | 5/2017 | Tally .................. A61B 17/1671 |
| 2003/0130660 A1 | 7/2003 | Levy et al. |
| 2004/0156879 A1* | 8/2004 | Muratoglu .............. A61L 27/16 424/423 |
| 2004/0182202 A1 | 9/2004 | Geving et al. |
| 2004/0226405 A1 | 11/2004 | Geving et al. |
| 2005/0228391 A1 | 10/2005 | Levy et al. |
| 2007/0065779 A1 | 3/2007 | Mangano |
| 2008/0269752 A1 | 10/2008 | Simon et al. |
| 2009/0005782 A1 | 1/2009 | Chirico et al. |
| 2009/0171452 A1 | 7/2009 | Yamamoto et al. |
| 2009/0281580 A1 | 11/2009 | Emannuel |
| 2010/0023012 A1 | 1/2010 | Voor |
| 2010/0076556 A1* | 3/2010 | Tomantschger ........ A61L 17/10 623/11.11 |
| 2010/0249850 A1* | 9/2010 | Cerynik .................. A61B 17/72 606/281 |
| 2010/0249900 A1 | 9/2010 | Sager et al. |
| 2010/0262089 A1* | 10/2010 | Sweeney ............ A61B 17/3472 604/272 |
| 2010/0268285 A1 | 10/2010 | Tipirneni et al. |
| 2010/0278891 A1* | 11/2010 | Ringeisen .............. A61B 17/80 424/422 |
| 2012/0109128 A1 | 5/2012 | Frigg |
| 2012/0184993 A1 | 7/2012 | Arambula et al. |
| 2013/0338756 A1 | 12/2013 | Gerold et al. |
| 2014/0031940 A1 | 1/2014 | Banouskou |
| 2014/0097277 A1 | 4/2014 | Kumta et al. |
| 2014/0178576 A1 | 6/2014 | Narasimhan et al. |
| 2017/0135706 A1* | 5/2017 | Frey ................... A61B 17/1703 |
| 2018/0065324 A1* | 3/2018 | Isobe ........................ B22F 1/00 |
| 2019/0134276 A1* | 5/2019 | Spiller .................. C09D 11/04 |

FOREIGN PATENT DOCUMENTS

| | | |
|---|---|---|
| CN | 201861742 U | 6/2011 |
| CN | 102512711 A | 6/2012 |
| CN | 103313737 A | 9/2013 |
| CN | 103585672 A | 2/2014 |
| CN | 104334503 A | 2/2015 |
| CN | 104694848 A | 6/2015 |
| EP | 1800700 A2 | 6/2007 |
| EP | 2777633 A2 | 9/2014 |
| TW | I513480 B | 12/2015 |
| TW | M522000 U | 5/2016 |
| TW | I576872 B | 4/2017 |
| TW | 201731464 A | 9/2017 |
| WO | WO 2004/094089 A1 | 11/2004 |
| WO | WO 2010/091242 A1 | 8/2010 |

OTHER PUBLICATIONS

Blumberg, Nehemia, et al., "The femoral head expandable peg: improved periimplant bone properties following expansion in a cadaveric model," Arch Orthop Trauma Surg, DOI 10.1007/s00402-006-0188-4, Trauma Surgery, 2006, 7 pgs., Springer-Verlag, Tel Aviv, Israel.

Ertem, F., et al., Abstract of "Biomechanical Assessment of a Novel Expandable Hip Screw Versus Dynamic Hip Screw," Jan. 5, 2018 Orthopaedic Proceedings, http://bjicrocs.boneandloint.org.uk/content/99-B/SUPP_9/38B/SUPP_9/38. May 8, 2017, 2 pgs., British Editorial Society of Bone & Joint Surgery, UK.

Zhang, Shaoxiang, et al., "Research on an Mg—Zn alloy as a degradable biomaterial," Acta Biomaterialia 6 (2010), Jun. 21, 2009, pp. 626-640, Elsevier Ltd.

Chen, Yongjun, et al., "Recent advances on the development of magnesium alloys for biodegradable implants," Acta Biomaterialia 10 (2014), Jul. 14, 2014, pp. 4561-4573, Elsevier Ltd.

Li, Haufang, et al., "Progress of biodegradable metals," Progress in Natural Science: Materials International 24 (2014), Oct. 30, 2014, pp. 414-422, Elsevier B.V.

Wang, Juan, "Preparation of Biodegradable iron-zinc Alloys by Electroforming and their Properties Investigation," Dalian University of Technology, 2014, 78 pgs. with English-language Abstract, Dalian, China.

Huang, Tao, et al., "Accelerating degradation rate of pure iron by zinc ion implantation," Regenerative Biomaterials, Jun. 5, 2016, pp. 205-215, Oxford University Press.

Lee, Jee-Wook, et al., "Long-term clinical study and multiscale analysis of in vivo biodegradation mechanism of Mg alloy," PNAS, vol. 113, No. 3, Jan. 19, 2016, pp. 716-721, PNAS.

Brar, Harpreet S., et al., "Magnesium as a Biodegradable and Bioabsorbable Material for Medical Implants," Biomedical Materials and Devices Overview, JOM (2009) 61: 31 (vol. 61, Issue 9, pp. 31-34), https://doi.org/10.1007/s11837-009-0129-0, Sep. 9, 2009, 9 pgs., Springer US.

Sheikh, Zeeshan, et al., "Biodegradable Materials for Bone Repair and Tissue Engineering Applications," Materials 2015, 8, Aug. 31, 2015, pp. 5744-5794, MDPI, Basel, Switzerland.

Schinhammer, Michael, et al., "On the cytocompatability of biodegradable Fe-based alloys," Material Science and Engineering C 33 (2013), Nov. 10, 2012, pp. 782-789, Elsevier B.V.

Li, Huafang, et al., "Progress of biodegradable metals," Progress in Natural Science: Materials International 24 (2014), Oct. 30, 2014, pp. 414-422, Elsevier B.V.

Liu, Xiwei, et al., "In vitro investigation of ultra-pure Zn and its mini-tube as potential bioabsorbable stent material," Materials Letters 161 (2015), Jul. 2, 2015, pp. 53-56, Elsevier B.V.

Zhu, Shengfa, et al., "Biocompatibility of Fe—O films synthesized by plasma immersion ion implantation and deposition," Surface & Coatings Technology 203 (2009), Dec. 6, 2008, pp. 1523-1529, Elsevier B.V.

(56) References Cited

OTHER PUBLICATIONS

Zheng, Y.F., et al., "Biodegradable metals," Materials Science and Engineering R 77 (2014), Mar. 6, 2014, pp. 1-34, Elsevier B.V.
Ishak, Dahaman, et al., "Eddy-Current Loss in the Rotor Magnets of Permanent-Magnet Brushless Machines Having a Fractional Number of Slots Per Pole," IEEE Transactions on Magnetics, vol. 41, No. 9, Sep. 2005, pp. 2462-2469, Sheffield, U.K.
Sung, Jeong-hyoun, et al., "A New Approach to Vector Control for a Linear Induction Motor Considering End Effects," Industry Applications Conference, 1999. Thirty-Fourth IAS Annual Meeting. Conference Record of the 1999 IEEE, Date of Conference Oct. 3-7, 1999, pp. 2284-2289, IEEE.
Yamazaki, Katsumi, et al., "Loss Analysis of Permanent Magnet Motors with Concentrated Windings—Variation of Magnet Eddy Current Loss Due to Stator and Rotor Shapes," IEEE Transactions on Industry Applications (vol. 45, Issue: 4, Jul.-Aug. 2009), May 19, 2009, pp. 1334-1342, 8 pgs., IEEE.
Zhang, Baicheng, et al., "Microstructure and Magnetic Properties of Fe—Ni Alloy Fabricated by Selective Laser Melting Fe/Ni Mixed Powders," J. Mater Sci. Technol., 2013, 29(8), May 22, 2013, pp. 757-760, Elsevier Limited.

\* cited by examiner

METHOD FOR FABRICATING MEDICAL DEVICE AND APPLICATIONS THEREOF

TECHNICAL FIELD

The disclosure relates in general to a method for fabricating a medical device and applications thereof; and more particularly to a method for fabricating a biodegradable medical device and applications thereof.

BACKGROUND

As the increase of the share of older individuals in a society due to fertility declines and rising life expectancy, population aging is an irreversible global trend, the medical expenses will grow continuously and the demand for medical implants will also increase. Typical medical implants, such as bone nails and bone plates used in an orthopedic surgery, are formed of metals (such as stainless steel, cobalt chromium alloy, titanium and titanium alloy) and have the advantages of high strength, high toughness, high fatigue resistance, high corrosion resistance, high plasticity, high workability and high economy. However, the metal medical implant does not degrade after being implanted in a human body, but has the potential risk of infection. Normally, after the wound heals, a second surgery is required to remove the metal medical implant from the body.

The second surgery for removing the medical implant has the clinical risk of causing complications and damaging nerves. Therefore, a new technology for fabricating a medical implant using biodegradable polymers and macromolecules such as polylactic acid (PLA), polyglycolic acid (PGA), polycyanoacrylate (PACA) is provided in response to the need. The medical implant formed of macromolecules can be absorbed by the human body and there is no need to perform a second surgery to remove it from the human body, hence avoiding causing extra risks and damages to the patient. However, the medical implant formed of biodegradable macromolecule materials still has the problems of lacking sufficient mechanical strength, having poor mechanical properties and high degradation rate, thus cannot be able to bear an excessive stress.

Therefore, it has become a prominent task for the pertinent industries to provide an advanced biodegradable medical device and a method for fabricating the same.

SUMMARY

According to one embodiment of the present disclosure, a method for fabricating a medical device is provided, wherein the method includes steps as follows: A biodegradable powder including at least one metal element is firstly provided onto a target surface. An energy bean moving along a predetermined path irradiates to heat the biodegradable powder and form a melted or sintered compositing material disposed on the target surface within an oxygen-containing atmosphere, when the energy bean is driven to move from a first location to a second location of the target surface, the oxygen-containing atmosphere can be adjusted to provide the first location and the second location a first oxygen concentration and a second oxygen concentration respectively. The same steps of irradiating an energy bean moving along a predetermined path to heat the biodegradable powder form a melted or sintered compositing material, as discussed above, are then repeatedly carried out to form a three-dimensional (3D) structure of the medical device.

According to another embodiment of the present disclosure, a medical device is provided, wherein the medical device is fabricated by the method as discussed above.

In according to the embodiments of the present disclosure, a biodegradable powder including at least one metal element and disposed on a target surface is sintered/melted in an oxygen-containing atmosphere; and the sintered/melted biodegradable powder is then cured to form a solid mass of compositing material (a melted or sintered compositing material) including at least one base metal and at least one metal oxide. During the sintering/melting processes, an energy bean moving along a predetermined path irradiates to sinter/melt the biodegradable powder form a melted or sintered compositing material, and the oxygen-containing atmosphere is adjusted to provide different oxygen concentrations to different locations on which the energy bean irradiates. The same steps of irradiating an energy bean moving along a predetermined path to heat the biodegradable powder form a melted or sintered compositing material, are then repeatedly carried out to form a 3D structure of the medical device. In some embodiments of the present disclosure, the medical device can be obtained by assembling a plurality of 3D components made of the melted or sintered compositing material or just a block constituted by the melted or sintered compositing material. In some other embodiments of the present disclosure, the medical device may include an unremovable substrate and at least one layer of the melted or sintered compositing material coated thereon.

In some embodiments of the present disclosure, different portions of the medical device respectively formed in the oxygen-containing atmosphere with different oxygen concentration may correspondingly have different contents of the metal oxide and the oxygen which may alter the biodegradable rates and mechanical properties thereof. The oxygen concentrations of the oxygen-containing atmosphere can be adjust corresponding to the location shift of the energy bean along the predetermined path, during the sintering/melting processes, to make a certain portion of the medical device having a certain oxygen and metal oxide contents. As a result, a biodegradable medical device having a desired mechanical property can be provided, and the problems of second surgery for removing the non-biodegradable medical implant or the problems of poor mechanical properties of the biodegradable medical device can be obviated.

BRIEF DESCRIPTION OF THE DRAWINGS

The disclosure can be more fully understood by reading the subsequent detailed description and examples with references made to the accompanying drawings, wherein.

DETAILED DESCRIPTION

According to the present disclosure, a method for fabricating a medical device and applications thereof are provided to solve the problems due to the second surgery for removing the non-biodegradable medical implant or the poor mechanical properties of a biodegradable medical device. Several embodiments of the present disclosure are disclosed below with reference to accompanying drawings.

However, the structure and content disclosed in the embodiments are for exemplary and explanatory purposes only, and the scope of protection of the present disclosure is not limited to the embodiments. Designations common to the accompanying drawings and embodiments are used to indicate identical or similar elements. It should be noted that the present disclosure does not illustrate all possible embodiments, and anyone skilled in the technology field of the invention will be able to make suitable modifications or changes based on the specification disclosed below to meet actual needs without breaching the spirit of the invention. The present disclosure is applicable to other implementations not disclosed in the specification. In addition, the drawings are simplified such that the content of the embodiments can be clearly described, and the shapes, sizes and scales of elements are schematically shown in the drawings for explanatory and exemplary purposes only, not for limiting the scope of protection of the present disclosure.

Figure 1A:
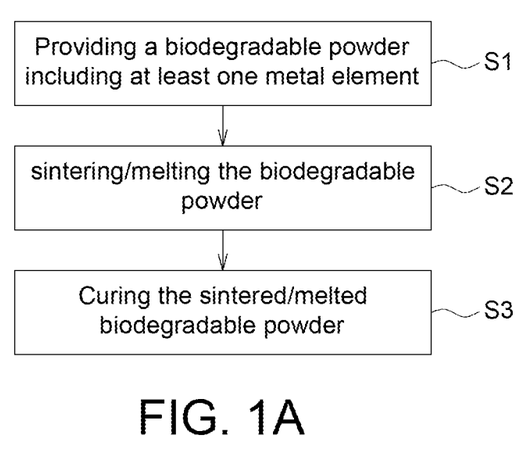
FIG. 1A is a flow chart illustrating a method and process for fabricating a medical device according to one embodiment of the present disclosure.
Figure 1B:
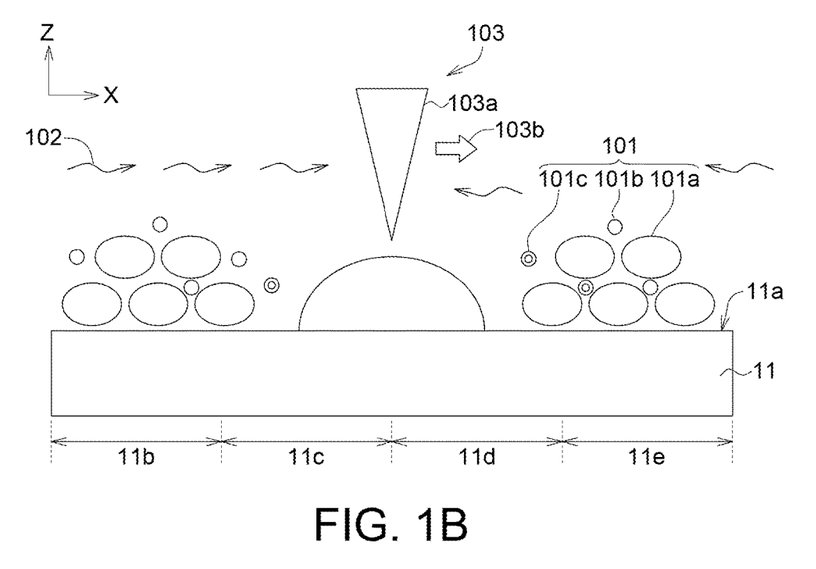
FIGS. 1B to 1C are cross-sectional views illustrating portions of the processing structures for fabricating a medical device using the method as depicted in FIG. 1A.
Figure 1C:
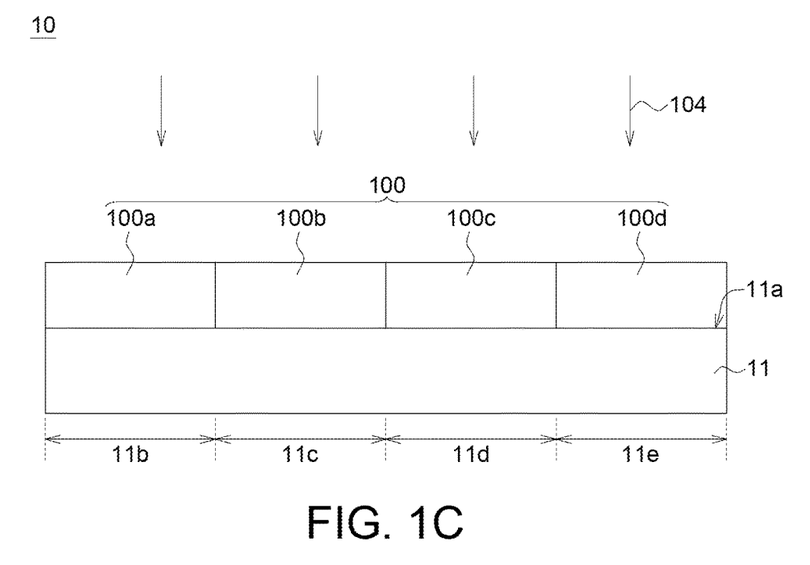

FIG. 1A is a flow chart illustrating a method and process for fabricating a medical device 10 according to one embodiment of the present disclosure; and FIGS. 1B to 1C are cross-sectional views illustrating portions of the processing structures for fabricating the medical device 10 using the method as depicted in FIG. 1A. The method for fabricating the medical device 10 includes steps as follows:

Firstly, a biodegradable powder 101 including at least one metal element is provided on a surface 11a of a substrate 11 (see step S1), wherein the substrate 11 may be a rigid/flexible board, plate or film, made of plastic, metal, ceramics, fabric, other suitable material or the arbitrary combinations thereof. In some embodiments, the substrate 11 may be an unremovablesubstrate, e.g. the blank body of a medical implant (such as a bone screw or bone plate) that can provide an unremovable basis for performing the following fabrication process and will not be removed thereafter. Alternatively, the substrate 11 may be a temporary substrate or a carrying substrate that should be removed after the fabrication process. In the present embodiment, the step of providing the biodegradable powder 101 on the surface 11a of the substrate 11 can be implemented by directly covering a layer of the biodegradable powder 101 onto the surface 11a of a rigid carrying substrate.

The biodegradable powder 101 may include at least one metal element selected from a group consisting of iron (Fe), calcium (Ca), magnesium (Mg), zinc (Zn), titanium (Ti) and the arbitrary combinations thereof. For example, in some embodiments of the present disclosure, the biodegradable powder 101 may include a Fe-based metal powder 101a and a ceramic-based powder 101b (such as a hydroxyapatite (HA) powder, a tricalcium phosphate (TCP) powder, a titanium oxide powder, an aluminum oxide powder, a silicon oxide powder, a zirconia oxide powder or the arbitrary combinations thereof).

The biodegradable powder 101 may further include a Fe-free metal powder 101c, such as a Mg powder, a Zn powder or the combination thereof. In the present embodiment, the biodegradable powder 101 may include the Fe-based metal powder 101a with a content greater than 80 percent by weight (such as 85%), the ceramic-based powder 101b with a content less than 20 percent by weight (such as 85%) and the Fe-free metal powder 101c (such as a Zn powder) with a content less than 5 percent by weight (such as 3%).

However, the contents or ingredient of the biodegradable powder 101 may not be limited to this regard. In some embodiments of the present disclosure, the biodegradable powder 101 can either only include the Fe-based metal powder 101a or only include the ceramic-based powder 101b. In one embodiment of the present disclosure, the biodegradable powder 101 can be the combination of the Fe-based metal powder 101a and at least one kind of the Fe-free metal powder 101c. In another embodiment of the present disclosure, the biodegradable powder 101 can be the combination of the ceramic-based powder 101b and at least one kind of the Fe-free metal powder 101c. In yet another embodiment of the present disclosure, the biodegradable powder 101 can be the combination of the Fe-based metal powder 101a and at least one kind of the ceramic-based powder 101b.

Next, the biodegradable powder 101 is subjected to a sintering/melting process 103 in an oxygen-containing atmosphere 102 (see step S2). In some embodiments of the present disclosure, the sintering/melting process 103 may include steps of irradiating an energy bean 103a moving along a predetermined path 103b to sinter/melt the biodegradable powder 101 disposed on the surface 11a of the substrate 11 within the oxygen-containing atmosphere 102. During sintering/melting process 103, the oxygen-containing atmosphere 102 can be adjusted to provide different oxygen concentrations, when the irradiating energy bean 103a shifts from one location to another. The oxygen concentrations provided by the oxygen-containing atmosphere 102 may range from 0.1 wt % to 25 wt %.

In the present embodiment, during the sintering/melting process 103, a laser beam (the energy bean 103a) with a power ranging from 200 Watts (W) to 340 W and a scanning speed ranging from 1500 micrometer per second (mm/s) to 4500 mm/s, is provided and irradiates to move along a direction parallel to the X axis for sintering and melting the biodegradable powder 101 disposed on the surface 11a of the substrate 11 within the oxygen-containing atmosphere 102. Except Oxygen gas ($O_2$), the oxygen-containing atmosphere 102 may further include at least one inert gas, such as argon (Ar), nitrogen gas ($N_2$) or the combination thereof.

When the energy bean 103a irradiates onto a first location 11b of the substrate surface 11a, the oxygen-containing atmosphere 102 can be adjusted by altering the relative flowing rate of the oxygen and inert gases to provide an oxygen concentration about 0.2 wt %; when the irradiating energy bean 103a shifts to a second location 11c of the substrate surface 11a, the oxygen-containing atmosphere 102 can be adjusted by the same way to provide an oxygen concentration about 1 wt %; when the irradiating energy bean 103a shifts to a third location 11d of the substrate surface 11a, the oxygen-containing atmosphere 102 can be adjusted by the same way to provide an oxygen concentration about 3 wt %; and when the irradiating energy bean 103a shifts to a forth location 11e of the substrate surface 11a, the oxygen-containing atmosphere 102 can be adjusted by the same way to provide an oxygen concentration about 5 wt %.

Thereinafter, an annealing treatment 104 is performed to cure the sintered/melted biodegradable powder 101 (see step S3), so as to form a layer of melted or sintered compositing material 100 on the surface 11a of the substrate 11 (see FIG. 1C). In some embodiments of the present disclosure, the annealing treatment 104 can be performed in an air atmosphere with a treating time about 0.5 hours (hrs) to 2 and an annealing temperature ranging from 300° C. to 600° C.

The melted or sintered compositing material 100 may has a grid structure or a plurality of pores (not shown). Since the biodegradable powder 101 used to form the melted or sintered compositing material 100 includes at least one kind of metal powder, thus at least one portion of the metal powder can be oxidized by the sintering/melting process 103. In other words, the melted or sintered compositing material 100 may include at least one kind of base metal that is not oxidized by the sintering/melting process 103 and at least one kind of metal oxide formed by the other portion of the oxidized metal powder that is oxidized by the sintering/melting process 103. In some embodiments of the present disclosure, the at least one kind of base metal involved in the melted or sintered compositing material 100 can be pure iron, iron alloy, Ti alloy, Mg alloy, Zn alloy or the arbitrary combinations thereof; and the metal oxide involved in the melted or sintered compositing material 100 can be oxides of iron, oxides of calcium, oxides of magnesium, oxides of zinc or the arbitrary combinations thereof.

In the present embodiment, during the sintering/melting process 103, the irradiating energy bean 103a can shift along the predetermined path 103b parallel to the X axis (parallel to the earth plane). And the compositing material compositing material 100 that is formed by the sintering/melting process 103 can be thus a flat layered structure extending along the X axis. The compositing material compositing material 100 can be divided into several continuous regions, such as a first region 100a, a second region 100b, a third region 100c and a forth region 100d corresponding to the first location 11b, the second location 11c, the third location 11e and the forth location 11f respectively. In addition, the first region 100a, the second region 100b, the third region 100c and the forth region 100d of the compositing material compositing material 100 that are respectively formed by sintering/melting the biodegradable powder 101 disposed on different locations (the first location 11b, the second location 11c, the third location 11e and the forth location 11f) using the energy bean 103a within atmosphere of different oxygen concentrations may include different contents of the metal oxide. In the present embodiment, the portions of the compositing material compositing material 100 respectively constituting the first region 100a, the second region 100b, the third region 100c and the forth region 100d may have different contents of the metal oxide, wherein the contents of the metal oxide may range from 0.1 wt % to 1 wt %.

Subsequently, the melted or sintered compositing material 100 is subjected to series downstream processes, such as cutting, shaping, pasting or the like (not shown), meanwhile the medical device 10 can be implemented.

Figure 2A:
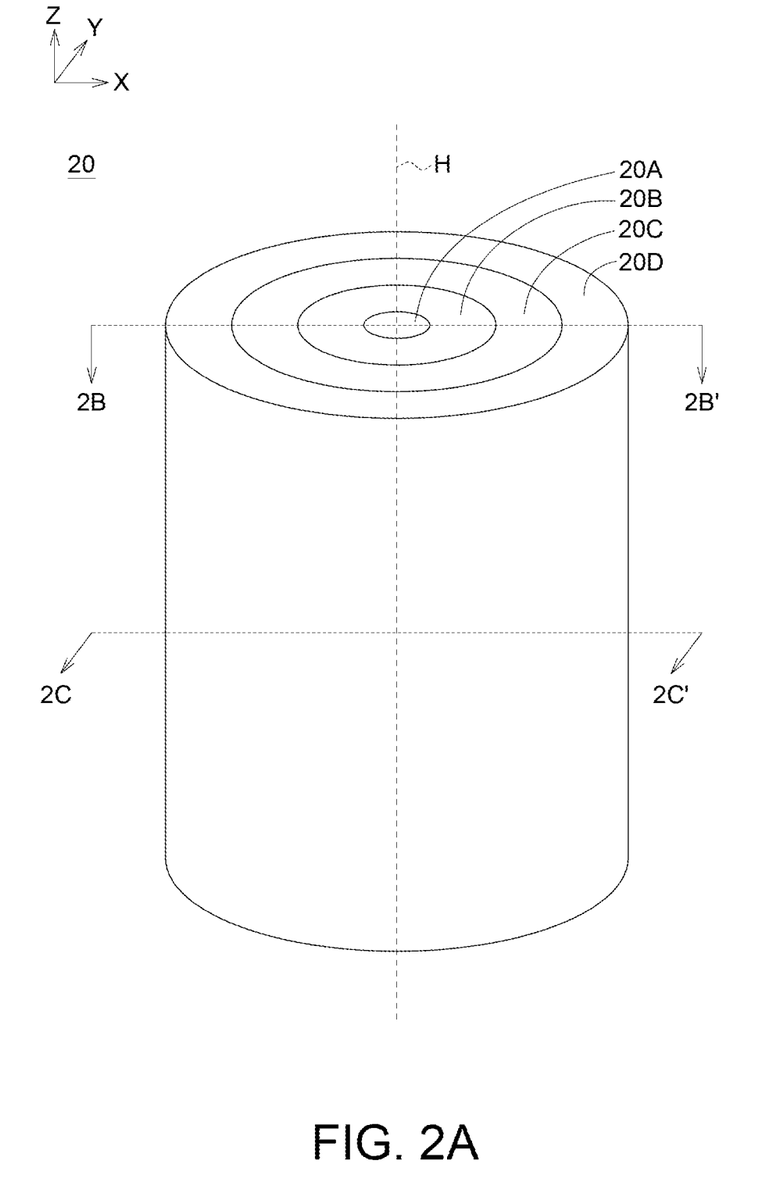
FIG. 2A is a prospective view illustrating a medical device according to another embodiment of the present disclosure.
Figure 2B:
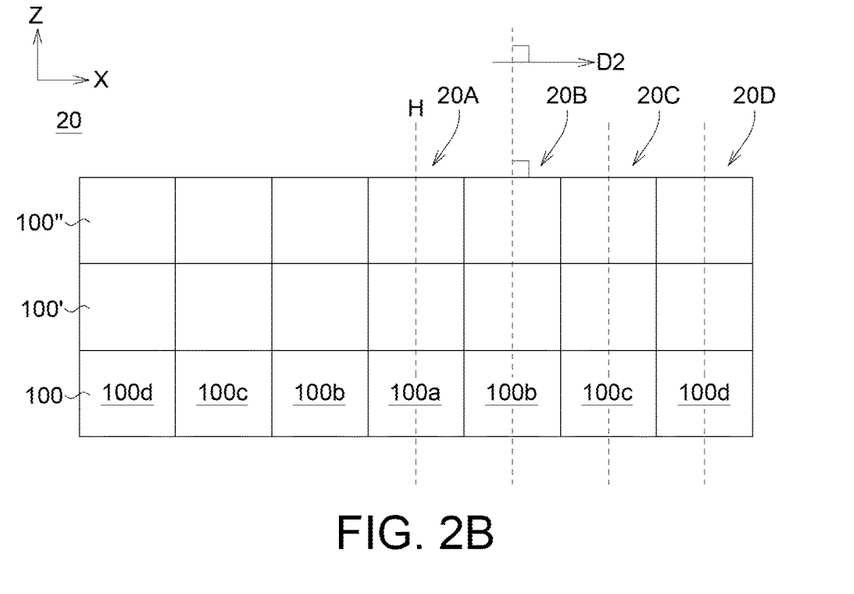
FIG. 2B is a cross-sectional view of the medical device taken along the section line 2B-2B' as depicted in FIG. 2A.
Figure 2C:
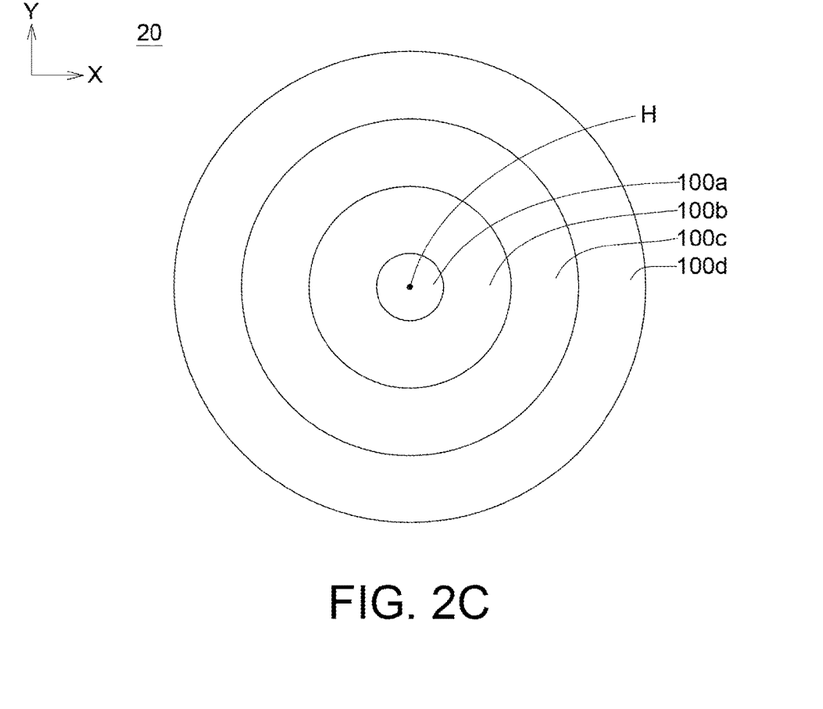
FIG. 2C is a cross-sectional view of the medical device taken along the section line 2C-2C' as depicted in FIG. 2A.

However, it should be appreciated that the structure of the medical device 10 may not be limited to this regard. For example, FIG. 2A is a prospective view illustrating a medical device 20 according to another embodiment of the present disclosure; FIG. 2B is a cross-sectional view of the medical device taken along the section line 2B-2B' as depicted in FIG. 2A; and FIG. 2C is a cross-sectional view of the medical device taken along the section line 2C-2C' as depicted in FIG. 2A. In the present embodiment, the medical device 20 may be implemented by repeating the steps S1 to S3 as described to form a plurality of round-shaped melted or sintered compositing material 100' and 100" stacked on the melted or sintered compositing material 100 along a direction substantially parallel to the Z axis, wherein the medical device 20 can be a cylindrical block (see FIG. 2A).

Each of the melted or sintered compositing material 100, 100' and 100" can be divided into four continuous regions, such as a first region 100a, a second region 100b, a third region 100c and a forth region 100d with different contents of the metal oxide, wherein the regions of the melted or sintered compositing material 100, 100' and 100" that are designated with the same reference number may align and connect with each other to form a plurality of region blocks (see FIG. 2B). In the present embodiment, the medical device 20 has a first region block 20A constituted by the first regions 100a, a second region block 20B constituted by the second regions 100b, a third region block 20C constituted by the first regions 100c and a forth region block 20D constituted by the second regions 100d radially arranged outwards from the central axis H of the cylindrical block to the edge thereof. In other words, they are arranged along a direction D2 perpendicular to the stack direction (which is parallel to the Z axis) of the melted or sintered compositing material 100, 100' and 100".

In the present embodiment, the metal oxide contents of the first region block 20A, the second region block 20B, the third region block 20C and the forth region block 20D, involved in the medical device 20 may be declined from the central axis H of the cylindrical block to the edge thereof. However, the distribution of the metal oxide contents cannot be limited to this regard. In one embodiment of the present disclosure, the metal oxide contents of the first region block 20A, the second region block 20B, the third region block 20C and the forth region block 20D, involved in the medical device 20 may be alternatively declined from the edge of the cylindrical block to the central axis H.

Figure 3A:
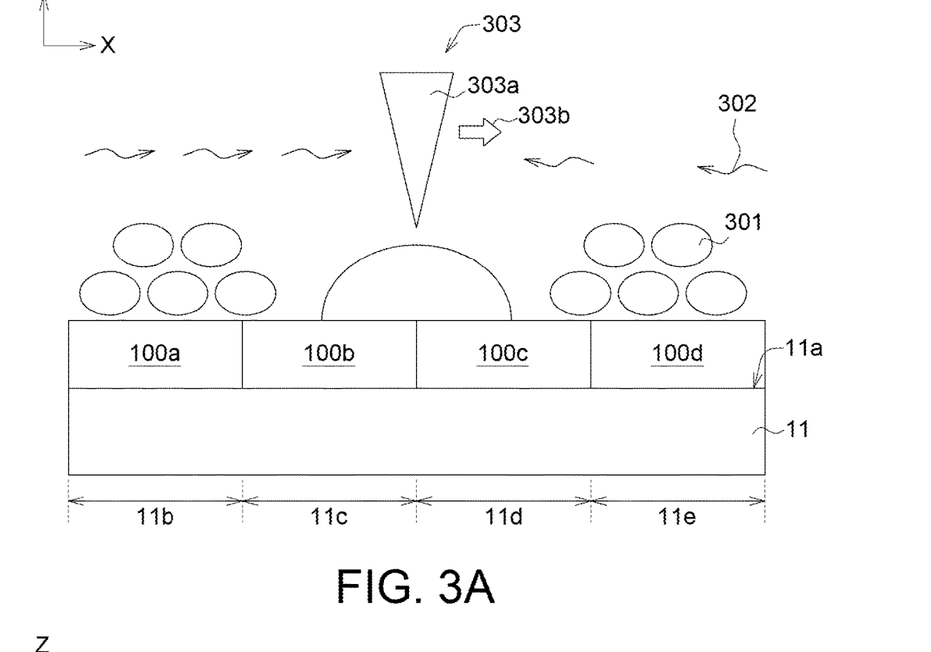
FIGS. 3A to 3B are cross-sectional views illustrating portions of the processing structures for fabricating a medical device according to yet another embodiment of the present disclosure.
Figure 3B:
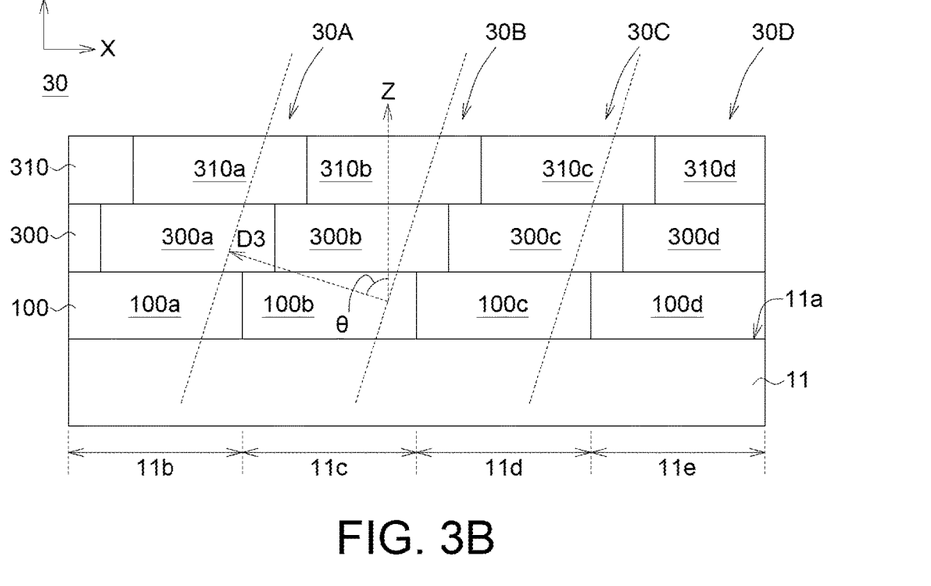

FIGS. 3A to 3B are cross-sectional views illustrating portions of the processing structures for fabricating a medical device 30 according to yet another embodiment of the present disclosure. The process and method for fabricating the medical device 30 are generally like that for fabricating the medical device 20, except that the predetermined path 103b and the oxygen concentrations can be dynamically altered while repeating the step S2. Such that, when the steps S1 and S3 are repeated for several times, a plurality of melted or sintered compositing material (such as the melted or sintered compositing material 300 and 310) with different shape and distribution of the metal oxide contents can be formed to vertically stack on the melted or sintered compositing material 100 parallel to the earth plane.

The method for fabricating the medical device 30 includes steps as follows: Firstly, a biodegradable powder 301 including at least one metal element is provided on the melted or sintered compositing material 100 as depicted in FIG. 1C. In some embodiments of the present disclosure, the biodegradable powder 301 may be identical to or different from the biodegradable powder 101 as described in FIG. 1B. In the present embodiment, the contents or ingredient of the biodegradable powder 301 may be identical to that of the biodegradable powder 101.

Next, the biodegradable powder 301 is subjected to a sintering/melting process 303 in an oxygen-containing atmosphere 302 (see FIG. 3A). In some embodiments of the present disclosure, the operating conditions and parameters of the energy bean 103a used to perform the sintering/melting process 303 can be adjusted according to the contents or ingredient of the biodegradable powder 301. The predetermined path 303b to sinter/melt the biodegradable powder 301 also can be altered according to the shape design of the medical device 30. The concentrations and relative flowing rate of the various active gases involved in the oxygen-containing atmosphere 302 can be dynamic adjusted during the sintering/melting process 303 to provide the medical device 30 various desirable materials on different predetermined locations for biodegradation.

Thereinafter, an annealing treatment 104 is performed to cure the sintered/melted biodegradable powder 101, so as to form a melted or sintered compositing material 100 including several continuous regions (such as, a first region 300a, a second region 300b, a third region 300c and a forth region 300d) on the melted or sintered compositing material 100 (see FIG. 3B). The processes as depicted in FIGS. 3A-3B are then repeated to form a melted or sintered compositing material 310 including several continuous regions (such as, a first region 310a, a second region 310b, a third region 310c and a forth region 310d) on the melted or sintered compositing material 300.

In the present embodiment, the first region 300a of the cured compositing material 300, the first region 100a of the melted or sintered compositing material 100 and the first region 310a of the melted or sintered compositing material 310 that have identical contents and ingredient are connected with each other to form a first region block 30A; the second region 300b of the melted or sintered compositing material 300, the second region 100b of the melted or sintered compositing material 100 and the second region 310b of the melted or sintered compositing material 310 that have identical contents and ingredient are connected with each other to form a second region block 30B; the third region 300c of the compositing material compositing material 300, the third region 100c of the compositing material compositing material 100 and the third region 310c of the compositing material compositing material 310 that have identical contents and ingredient are connected with each other to form a third region block 30C; and the forth region 300d of the compositing material compositing material 300, the forth region 100d of the compositing material compositing material 100 and the forth region 310d of the compositing material compositing material 310 that have identical contents and ingredient are connected with each other to form a forth region block 30D; wherein the first region block 30A, the second region block 30B, the third region block 30C and the forth region block 30D, involved in the medical device 30 may have different contents of the metal oxide and oxygen.

The first regions 300a, 100a and 310a that constitute the first region block 30A fail to thoroughly align with each other. Similarly, the second regions 300b, 100b and 310b that constitute the second region block 30B; the third regions 300c, 100c and 310c that constitute the third region block 30C; and the forth regions 300d, 100d and 310d that constitute the forth region block 30D also fail to thoroughly align with each other. Such that, each of the first region block 30A, the second region block 30B, the third region block 30C and the forth region block 30D may tilt along a direction D3 that may form a non-straight angle Θ with the stack direction (which is parallel to the Z axis) of the compositing material compositing material 100, 100' and 100" (see FIG. 3C).

In some other embodiment, the first region 300a of the compositing material compositing material 300, the first region 100a of the compositing material compositing material 100 and the first region 310a of the compositing material compositing material 310 that have identical contents and ingredient may not connect with each other; the second region 300b of the compositing material compositing material 300, the second region 100b of the compositing material compositing material 100 and the second region 310b of the compositing material compositing material 310 that have identical contents and ingredient may not connect with each other; the third region 300c of the compositing material compositing material 300, the third region 100c of the cured compositing material 100 and the third region 310c of the compositing material compositing material 310 that have identical contents and ingredient may not connect with each other; and the forth region 300d of the compositing material compositing material 300, the forth region 100d of the compositing material compositing material 100 and the forth region 310d of the compositing material compositing material 310 that have identical contents and ingredient may not connect with each other.

Figure 4A:
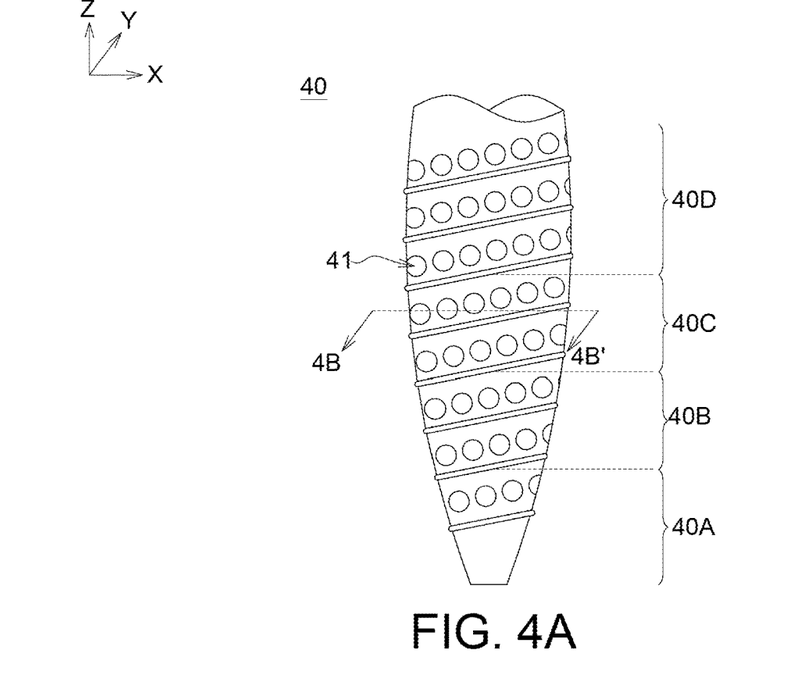
FIG. 4A is a prospective view illustrating a medical device according to yet another embodiment of the present disclosure.
Figure 4B:
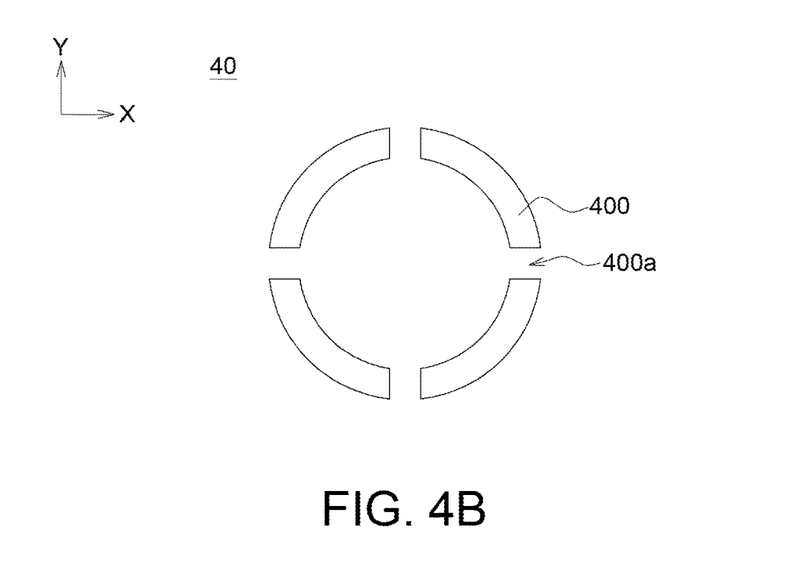
FIG. 4B is a cross-sectional view of the medical device taken along the section line 4B-4B' as depicted in FIG. 4A.

FIG. 4A is a prospective view illustrating a medical device 40 according to yet another embodiment of the present disclosure; and FIG. 4B is a cross-sectional view of the medical device taken along the section line 4B-4B' as depicted in FIG. 4A. The medical device 40 is formed by performing the process as described in FIG. 3A to, during which the predetermined path 303b as well as the concentrations and the relative flowing rate of the various active gases involved in the oxygen-containing atmosphere 302 are dynamic adjusted according the shape design of the medical device 40. In the present embodiment, the medical device 40 may have a tapered tubular structure including a first region block 40A, a second region block 40B, a third region block 40C and a forth region block 40D arranged along a direction parallel to the Z axis, wherein the first region block 40A, the second region block 40B, the third region block 40C and the forth region block 40D may have different contents of the metal oxide and oxygen. In one embodiment of the present disclosure, the medical device 40 may serve as a bone nail used in an orthopedic surgery.

The shape and profile of the medical device 40 can be altered by adjusting the predetermined path as well as the concentrations and the relative flowing rate of the various active gases involved in the oxygen-containing atmosphere during the process for fabricating the same. For example, in the present embodiment, the predetermined path for forming the compositing material compositing material 400 that is used to constitute the first region block 40A (the second region block 40B, the third region block 40C or the forth region block 40D) of the medical device 40 can be altered to make the compositing material compositing material 400 having at least one opening 401. Such that, each of the first region block 40A, the second region block 40B, the third region block 40C and the forth region block 40D of the medical device 40 can have at least one through hole 41 resulted by the opening 401 to improve the biodegradation rate of the medical device 40.

A biodegradation test, an acute toxicity test (e.g. assessing cell metabolic activity by a MTT assay) and a hardness test respectively according to International Standard ISO. 10993-1, "Biological evaluation of medical devices—Part 1: Evaluation and testing within a risk management process", and American Society for Testing and Materials (ASTM) standards, ASTM E18, ASTM E10 and ASTM E384, are performed to assess the biodegradability, the acute toxicity and the hardness of the blocks that have structure and material identical to that of the first region block 20A, the second region block 20B, the third region block 20C and the forth region block 20D. A Fe-based block that is made by the same sintering/melting processes within an inert atmosphere may be subjected to these tests serving as a scientific control group.

In according to the test results, the first region block 20A, the second region block 20B, the third region block 20C and the forth region block 20D of the medical device 20 may not adversely affect the cell lines; and the cell survival rate or cell inhibition percentage may be greater than about 70%. The biocompatibility of the first region block 20A, the second region block 20B, the third region block 20C and the forth region block 20D can be better than that of the Fe-based block. The hardness of the first region block 20A, the second region block 20B, the third region block 20C and the forth region block 20D can be rather similar to that of the Fe-based block and far more than that of the block made of biodegradable polymer material.

In addition, the test results also reveal that the contents of the metal oxide and the oxygen involved in the first region block 20A, the second region block 20B, the third region block 20C and the forth region block 20D of the medical device 20 can affect its biodegradability, wherein the more oxygen content the first region block 20A, the second region block 20B, the third region block 20C or the forth region block 20D has, the greater biodegradation rates it obtains. For example, in the present embodiment, the forth region block 20D that has the highest oxygen content can have a biodegradation rates about 0.692 micrometer per year (mm/year); and the first region block 20A that has the lowest oxygen content can have a biodegradation rate about 0.105 mm/year. In sum, the forth region block 20D has a biodegradability 3.6 times compared with that of the first region block 20A, which is 4 times compared with the biodegradation rate of the Fe-based block.

In according to the embodiments of the present disclosure, a biodegradable powder including at least one metal element and disposed on a target surface is sintered/melted in an oxygen-containing atmosphere; and the sintered/melted biodegradable powder is then cured to form a solid mass of compositing material (a compositing material compositing material) including at least one base metal and at least one metal oxide. During the sintering/melting process, an energy bean moving along a predetermined path irradiates to sinter/melt the biodegradable powder form a melted or sintered compositing material, and the oxygen-containing atmosphere is adjusted to provide different oxygen concentrations to different locations on which the energy bean irradiates. The same steps of irradiating an energy bean moving along a predetermined path to heat the biodegradable powder form a melted or sintered compositing material, are then repeatedly carried out to form a 3D structure of the medical device. In some embodiments of the present disclosure, the medical device can be obtained by assembling a plurality of 3D components made of the compositing material compositing material or just a block constituted by the compositing material compositing material. In some other embodiments of the present disclosure, the medical device may include an unremovable substrate and at least one layer of the compositing material compositing material coated thereon.

In some embodiments of the present disclosure, different portions of the medical device respectively formed in the oxygen-containing atmosphere with different oxygen concentration may correspondingly have different contents of the metal oxide and the oxygen which may alter the biodegradable rates and mechanical properties thereof. The oxygen concentrations of the oxygen-containing atmosphere can be adjust corresponding to the location shift of the energy bean along the predetermined path, during the sintering/melting processes, to make a certain portion of the medical device having a certain oxygen and metal oxide contents. As a result, a biodegradable medical device having a desired mechanical property can be provided, and the problems of second surgery for removing the non-biodegradable medical implant or the problems of poor mechanical properties of the biodegradable medical device can be obviated.

While the invention has been described by way of example and in terms of the preferred embodiment(s), it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A method for fabricating a medical device comprising:
providing a biodegradable powder comprising at least one metal element onto a target surface;
irradiating an energy beam moving along a predetermined path to heat the biodegradable powder to form a melted or sintered con/positing material disposed on the target surface within an oxygen-containing atmosphere, when the energy beam is driven to move from a first location to a second location of the target surface, the oxygen-containing atmosphere is adjusted to respectively provide the first location and the second location a first oxygen concentration and a second oxygen concentration; and
repeating steps of irradiating an energy beam moving along a predetermined path to heat the biodegradable powder to form a melted or sintered compositing material to form a three-dimensional (3D) structure.

2. The method according to claim 1, wherein the first oxygen concentration and the second oxygen concentration range from 0.1 wt % to 25 wt %.

3. The method according to claim 1, wherein the first location and the second location of the 3D structure respectively have a first oxygen content and a second oxygen content; and the first oxygen content and the second oxygen content range from 0.1 wt % to 1 wt %.

4. The method according to claim 1, wherein the at least one metal element is selected from a group consisting of iron (Fe), calcium (Ca), magnesium (Mg), zinc (Zn), titanium (Ti) and arbitrary combinations thereof.

5. The method according to claim 1, wherein the biodegradable powder comprises:
at least one of a Fe-based metal powder and a ceramic-based powder; and
a Fe-free metal powder, selected from a group consisting of a Mg powder, a Zn powder and a combination thereof.

6. The method according to claim 5, wherein the ceramic-based powder is selected from a group consisting of a hydroxyapatite (FIA) powder, a tricalcium phosphate (TCP) powder, a titanium oxide powder, an aluminum oxide powder, a silicon oxide powder, a zirconia oxide powder and arbitrary combinations thereof.

7. The method according to claim 1, wherein the target surface is disposed on either an unremovable substrate or a removable substrate.

8. A medical device fabricated by the method according to claim 1.

9. The medical device according to claim 8, wherein the first oxygen concentration and the second oxygen concentration range from 0.1 wt % to 25 wt %.

10. The medical device according to claim 8, wherein the first location and the second location of the 3D structure respectively have a first oxygen content and a second oxygen content; and the first oxygen content and the second oxygen content range from 0.1 wt % to 1 wt %.

11. The medical device according to claim 8, wherein the at least one metal element is selected from a group consisting of Fe, Ca, Mg, Zn, Ti and arbitrary combinations thereof.

12. The medical device according to claim 8, wherein the biodegradable powder comprises:
    at least one of a Fe-based metal powder and a ceramic-based powder; and
    a Fe-free metal powder, selected from a group consisting of a Mg powder, a Zn powder and a combination thereof.

13. The medical device according to claim 8, wherein the ceramic-based powder is selected from a group consisting of a HA powder, a TCP powder, a titanium oxide powder, an aluminum oxide powder, a silicon oxide powder, a zirconia oxide powder and arbitrary combinations thereof.

14. The medical device according to claim 8, wherein the target surface is disposed on either an unremovable substrate or a removable substrate.

15. The medical device according to claim 8, wherein the melted or sintered compositing material comprises at least one base metal and at least one metal oxide; and a portion of the melted or sintered compositing material disposed on the first location and a portion of the melted or sintered compositing material disposed on the second location have different contents of the at least one base metal and the at least one metal oxide.

16. The medical device according to claim 15, wherein the base metal is selected from a group consisting of oxides of pure iron, iron alloy, Ti alloy, Mg alloy, Zn alloy and arbitrary combinations thereof.

17. The medical device according to claim 15, wherein the least one metal is selected from a group consisting of oxides of iron, oxides of calcium, oxides of magnesium, oxides of zinc and arbitrary combinations thereof.

18. The medical device according to claim 15, wherein the melted or sintered compositing material further comprises a biocompatible ceramic material resulted from a ceramic-based powder.

19. The medical device according to claim 15, wherein the 3D structure comprises at least one through hole.

* * * * *